United States Patent [19]

McKenzie et al.

[11] Patent Number: 4,529,736

[45] Date of Patent: Jul. 16, 1985

[54] 3A-(SUBSTITUTED PHENYL)-2,3,3A,4,7,7A-HEXAHYDRO[OR 3A-(SUBSTITUTED-PHENYL)OCTAHYDRO]-4,7-ALKANO-1H-ISOINDOLES FOR TREATING DEPRESSION IN WARM-BLOODED ANIMALS

[75] Inventors: Thomas C. McKenzie, Tuscaloosa, Ala.; William J. Fanshawe, Pearl River; Joseph W. Epstein, Monroe, both of N.Y.

[73] Assignee: American Cyanamid Company, Stamford, Conn.

[21] Appl. No.: 480,541

[22] Filed: Apr. 6, 1983

Related U.S. Application Data

[63] Continuation-in-part of Ser. No. 467,576, Feb. 17, 1983, which is a continuation-in-part of Ser. No. 402,494, Jul. 28, 1982.

[51] Int. Cl.$^3$ .................... A61K 31/40; C07D 487/00
[52] U.S. Cl. ..................................... 514/411; 548/427
[58] Field of Search ..................... 548/427; 424/274

[56]  References Cited

U.S. PATENT DOCUMENTS 4,001,248  1/1977  Zimmerman et al. ............. 424/258
4,042,707  8/1977  Ripka ................................. 548/465

FOREIGN PATENT DOCUMENTS 898590   6/1962   United Kingdom ............... 548/465
1133778  11/1968  United Kingdom ............... 424/274
550384   3/1977   U.S.S.R. ............................. 424/274

OTHER PUBLICATIONS

McKenzie et al., Chem. Abst. 100-191735j.
Ripka, Chem. Abst., vol. 87, 1977, p. 562, 167879b.

Primary Examiner—Donald G. Daus
Assistant Examiner—Cecilia Shen
Attorney, Agent, or Firm—Edward A. Conroy, Jr.

[57]   ABSTRACT

This disclosure describes 3a-(substituted-phenyl)-2,3,3a,4,7,7a-hexahydro[or 3a-(substituted-phenyl)octahydro]-4,7-alkano-1H-isoindoles which possess activity as antidepressants and as antistress agents in mammals.

24 Claims, No Drawings

3A-(SUBSTITUTED PHENYL)-2,3,3A,4,7,7A-HEXAHYDRO[OR 3A-(SUBSTITUTED-PHENYL)OCTAHYDRO]-4,7-ALKANO-1H-ISOINDOLES FOR TREATING DEPRESSION IN WARM-BLOODED ANIMALS

CROSS REFERENCE TO RELATED APPLICATION

This application is a continuation-in-part of our co-pending application Ser. No. 467,576, filed Feb. 17, 1983, which is a continuation-in-part of our copending application Ser. No. 402,494, filed July 28, 1982.

BRIEF SUMMARY OF THE INVENTION

This invention relates to new organic compounds and, more particularly, is concerned with novel hexahydro(or octahydro)-alkanoisoindoles which may be represented by the following structural formula:

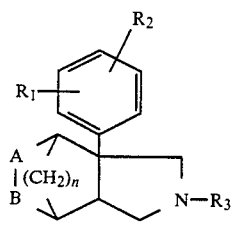

wherein n is an integer from 1 to 3; the moiety —A—B— is —CH=CH— or —CH$_2$CH$_2$—; R$_1$ and R$_2$ are each individually selected from the group consisting of hydrogen, hydroxy, alkyl having up to 3 carbon atoms, alkoxy having up to 3 carbon atoms, nitro, halo, trifluoromethyl, amino and azido; R$_3$ is hydrogen or alkyl having up to 3 carbon atoms; and R$_1$ and R$_2$ taken together are methylenedioxy or —CH$_2$CH$_2$CH$_2$CH$_2$—; and the pharmacologically acceptable acid-addition and quaternary ammonium salts thereof.

A preferred embodiment of the present invention consists of those compounds wherein n is 1 or 2; —A—B— is —CH$_2$CH$_2$—; R$_1$ and R$_2$ are both chloro and are substituted at the 3 and 4 positions of the phenyl ring; and R$_3$ is selected from the group consisting of hydrogen, methyl and ethyl.

DETAILED DESCRIPTION OF THE INVENTION

The novel organic free base compounds of the present invention are generally obtainable as viscous liquids, oils or solids ranging in description from colorless to yellow, and red thru brown. They have characteristic adsorption spectra and boiling points, and may be purified by selective distillation in vacuo. They are appreciably soluble in many organic solvents such as diethyl ether, ethyl acetate, dichloromethane, toluene and the like but are relatively insoluble in water. The organic free bases of this invention form non-toxic acid-addition salts with a variety of pharmacologically acceptable organic and inorganic salt-forming reagents. Thus, acid-addition salts, formed by admixture of the organic free base with one or two equivalents of an acid, suitably in a netural solvent, are formed with such acids as sulfuric, phosphoric, hydrochloric, hydrobromic, sulfamic, citric, lactic, malic, maleic, fumaric, succinic, tartaric, acetic, benzoic, gluconic, ascorbic, and the like. The acid-addition salts are generally obtainable as white, gray or yellow crystalline materials having characteristic melting points and absorption spectra and which may be crystallized in a solvent or combination of solvents such as acetone, ethanol, ethyl acetate, diethyl ether-acetonitrile, diethyl ether-hexane and the like. The acid-addition salts are relatively insoluble in non-polar organic solvents such as diethyl ether, benzene, toluene and the like but are appreciably soluble in water. For purposes of this invention, the free bases are equivalent to their non-toxic acid-addition salts.

The quaternary salts may be obtained by the combination of the free base with an alkyl halide such as methyl iodide, or a dialkyl sulfate such as dimethyl sulfate to give the quaternary salt compounds as crystalline solids, which are soluble in polar solvents.

The novel compounds of the present invention may be readily prepared in accordance with the following reaction scheme:

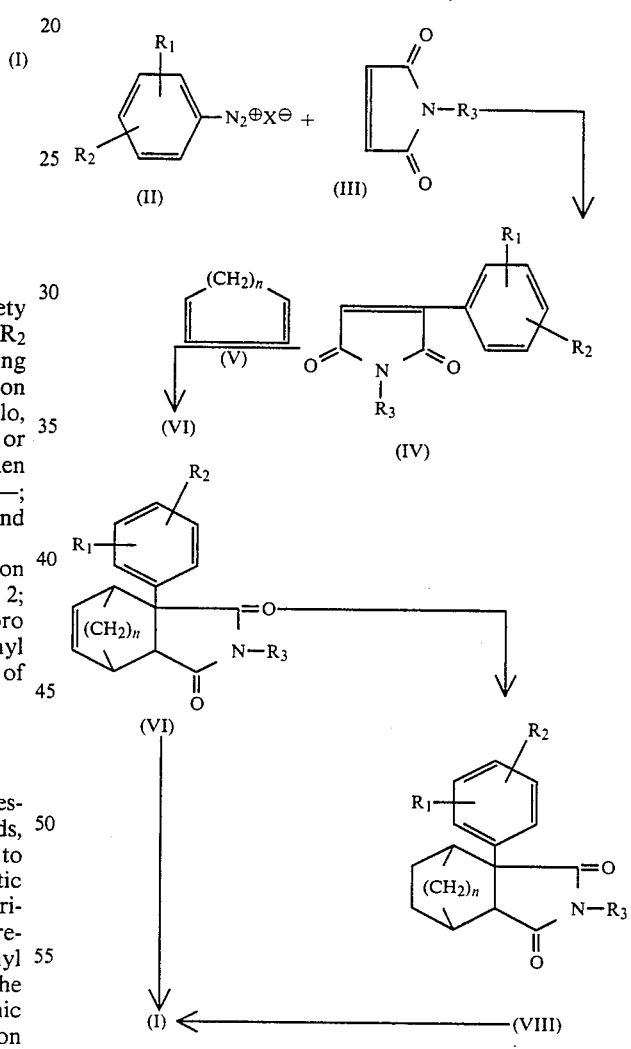

wherein X is chloro or bromo and n, R$_1$, R$_2$ and R$_3$ are as hereinbefore defined. In accordance with the above reaction scheme, an appropriately substituted benzenediazonium salt (II) is reacted with a maleimide (III) by the method of P. T. Izzo, J. Org. Chem., 28, 1713 (1963) to give the 2-(substituted-phenyl)maleimide (IV). This maleimide (IV) is reacted with cyclopentadiene, cyclohexadiene or cycloheptadiene (V) in dichloromethane at ambient temperatures-180° C. for 10–30 hours to provide the corresponding 2-(substituted-phenyl)bicycloalkene-dicarboximide (VI). The reaction of butadiene with 2-phenylmaleimides is disclosed in U.S. Pat. No. 4,042,707 and the reaction of simple maleimides with cyclopentadiene has been described by K. F. Hebenbrock in Liebigs Ann. Chem., 320 (1978). The bicycloalkene-dicarboximide (VI) is then reduced with VITRIDE ®T [a 70% solution of sodium dihydrobis(2-methoxyethoxy)aluminate in toluene] at room temperature for 2–4 hours followed by heating at reflux for 10–30 hours. Quenching of the reaction mixture by the addition of aqueous base followed by extraction into an organic solvent such as diethyl ether and work-up of the extract provides the compounds of the invention (I) where —A—B— is —CH=CH—. Alternatively, the bicycloalkene-dicarboximide (VI) may be reduced by catalytic hydrogenation to the corresponding 2-(substituted-phenyl)bicycloalkane-dicarboximide (VII). This reduction may be carried out with noble metal catalysts such as platinum oxide or palladium-on-carbon in an inert organic solvent such as ethyl acetate at room temperature and a few atmospheres pressure. The bicycloalkane-dicarboximide (VII) is then reduced with borane in tetrahydrofuran at the reflux for 12–24 hours, quenched by the addition of aqueous acid and the compounds of the invention (I) where —A—B— is —CH$_2$CH$_2$— are isolated by adding base to the aqueous solution and extracting with an organic solvent such as methylene chloride.

The compounds of this invention are useful as antidepressant agents in warm-blooded animals as verified by the following test. The antidepressant properties of these compounds were tested by measuring their ability to counteract depression induced in animals by the administration of tetrabenazine methanesulfonate. Each test compound was administered orally (P.O.) or intraperitoneally (I.P.) to 10 mice at a dose of 25 mg/kg of body weight. Thirty minutes later, tetrabenazine methanesulfonate was administered intraperitoneally to each mouse at a dose of 39 mg/kg of body weight, which dose is known to depress markedly the exploratory behaviour of normal mice. Thirty minutes later the mice were tested for their exploratory behaviour as described by E. Greenblatt and A. C. Osterberg, Toxicology and Applied Pharmacology, 7, 566–578 (1965). The results of this test on representative compounds of this invention appear in Table I.

TABLE I

| Tetrabenazine Induced Depression | | |
|---|---|---|
| Compound | Route | % Mice Protected |
| 3a(4-chlorophenyl)-2,3,3a,4,7,7a-hexahydro-4,7-methano-1H—isoindole fumarate | I.P. | 60 |
| octahydro-3a-phenyl-4,7-methano-1H—isoindole fumarate | I.P. | 50 |
| 2,3,3a,4,7,7a-hexahydro-2-methyl-3a-(4-methylphenyl)-4,7-methano-1H—isoindole maleate (1:1) | I.P. | 80 |
| 2,3,3a,4,7,7a-hexahydro-3a-(3-methoxyphenyl)-2-methyl-4,7-methano-1H—insoindole maleate (1:1) | P.O. | 40 |
| 3-(1,2,3,4,7,7a-hexahydro-2-methyl-4,7-methano-3aH—isoindol-3a-yl)phenol | P.O. | 60 |
| 2,3,3a,4,7,7a-hexahydro-2-methyl-3a-[3-(trifluoromethyl)phenyl]-4,7-methano-1H—isoindole fumarate | I.P. | 70 |
| 3a-(3,4-dichlorophenyl)octahydro-2-methyl-4,7-methano-1H—isoindole hydrochloride | I.P. | 60 |
| 4-(1,2,3,4,7,7a-hexahydro-2-methyl-4,7-methano-3aH—isoindol-3a-yl)benzenamine fumarate (1:2) | P.O. | 70 |
| 3a-(4-azidophenyl)octahydro-2,2-dimethyl-4,7-methano-1H—isoindolium iodide | P.O. | 30 |
| octahydro-2-methyl-3a-(4-nitrophenyl)-4,7-methano-1H—isoindole fumarate (1:1) | I.P. | 30 |
| 4-(1,2,3,4,5,6,7,7a-octahydro-2-methyl-4,7-methano-3aH—isoindol-3a-yl)benzenamine fumarate (1:1) | I.P. | 50 |
| 3a-(4-chlorophenyl)octahydro-2-methyl-4,7-methano-1H—isoindole fumarate (1:1) | I.P. | 60 |
| 3a-(3,4-difluorophenyl)octahydro-2-methyl-4,7-methano-1H—isoindole fumarate (1:1) | I.P. | 50 |
| 3a-(3-chlorophenyl)-2,3,3a,4,7,7a-hexahydro-2-methyl-4,7-methano-1H—isoindole fumarate (1:1) | I.P. | 60 |
| 3a-(3,4-dichlorophenyl)octahydro-2-methyl-4,7-ethano-1H—isoindole fumarate (1:1) | P.O. | 50 |
| 3a-(3,4-dichlorophenyl)-2-ethyl-octahydro-4,7-ethano-1H—isoindole fumarate (1:1) | P.O. | 50 |
| 3a-(3,4-dichlorophenyl)octahydro-4,7-methano-1H—isoindole hydrochloride | P.O. | 40 |

The antidepressant activity of the compounds of this invention was further established in the following test. Inhibition of tetrabenazine-induced ptosis is observed concomitantly with the inhibition of tetrabenazine-induced depression. Ptosis is defined as more than 75% closure of palpebral aperture induced in animals by the administration of tetrabenazine methanesulfonate. The compounds were administered orally (P.O.) or intraperitoneally (I.P.) at 25 mg/kg to groups of 10 mice. Thirty minutes later, tetrabenazine methanesulfonate was administered intraperitoneally to each mouse at a dose of 39 mg/kg. Thirty minutes after the injection of tetrabenazine, the mice were placed on an observation disc and examined for 10 seconds for inhibition of ptosis. Mice exhibiting 75% or greater opening of palpebral aperture are considered responders. The results of this test representative compounds of this invention appear in Table II.

TABLE II

| Tetrabenazine Induced Ptosis | | |
|---|---|---|
| Compound | Route | % Mice Responding |
| 3a(4-chlorophenyl)-2,3,3a,4,7,7a-hexahydro-4,7-methano-1H—isoindole fumarate | P.O. | 80 |
| octahydro-3a-phenyl-4,7-methano-1H—isoindole fumarate | I.P. | 50 |
| 2,3,3a,4,7,7a-hexahydro-2-methyl-3a-(4-methylphenyl)-4,7-methano-1H—isoindole maleate (1:1) | P.O. | 90 |
| 2,3,3a,4,7,7a-hexahydro-3a-(4-methylphenyl)-4,7-methano-1H—isoindole maleate (1:1) | I.P. | 60 |
| 2,3,3a,4,7,7a-hexahydro-3a-(3-methoxyphenyl)-2-methyl-4,7-methano-1H—insoindole maleate (1:1) | P.O. | 60 |
| 3-(1,2,3,4,7,7a-hexahydro-2-methyl-4,7-methano-3aH—isoindol-3a-yl)phenol | P.O. | 100 |
| 2,3,3a,4,7,7a-hexahydro-2-methyl-3a-[3-(trifluoromethyl)phenyl]-4,7-methano-1H—isoindole fumarate | I.P. | 100 |
| 3a-(3,4-dichlorophenyl)octahydro-2- | I.P. | 100 |

TABLE II-continued

Tetrabenazine Induced Ptosis

| Compound | Route | % Mice Responding |
|---|---|---|
| methyl-4,7-methano-1H—isoindole hydrochloride | | |
| 4-(1,2,3,4,7,7a-hexahydro-2-methyl-4,7-methano-3aH—isoindol-3a-yl)benzenamine fumarate (1:2) | I.P. | 100 |
| 3a-(4-azidophenyl)octahydro-2,2-dimethyl-4,7-methano-1H—isoindolium iodide | P.O. | 100 |
| octahydro-2-methyl-3a-(4-nitrophenyl)-4,7-methano-1H—isoindole fumarate (1:1) | I.P. | 70 |
| 4-(1,2,3,4,5,6,7,7a-octahydro-2-methyl-4,7-methano-3aH—isoindol-3a-yl)benzenamine fumarate (1:1) | I.P. | 100 |
| 3a-(4-chlorophenyl)octahydro-2-methyl-4,7-methano-1H—isoindole fumarate (1:1) | I.P. | 90 |
| 3a-(3,4-difluorophenyl)octahydro-2-methyl-4,7-methano-1H—isoindole fumarate (1:1) | I.P. | 70 |
| 3a-(3-chlorophenyl)-2,3,3a,4,7,7a-hexahydro-2-methyl-4,7-methano-1H—isoindole fumarate (1:1) | I.P. | 100 |
| 3a-(3,4-dichlorophenyl)octahydro-2-methyl-4,7-ethano-1H—isoindole fumarate (1:1) | I.P. | 90 |
| 3a-(3,4-dichlorophenyl)-2-ethyloctahydro-4,7-ethano-1H—isoindole fumarate (1:1) | I.P. | 100 |
| 3a-(3,4-dichlorophenyl)octahydro-4,7-methanol-1H—isoindole hydrochloride | I.P. | 100 |

The activity of the compounds of this invention as antidepressant agents was further verified in the following test which measures the ability of a test compound to inhibit [$^3$H]-imipramine binding to human platelet membranes.

Human platelet concentrates were diluted 1:20 with antiprotease containing buffer of the following composition:

0.12M sodium chloride
0.05M tris buffer
0.005N potassium chloride
0.025 μ/ml aprotinin
0.5 μg/ml pepstatin
$2 \times 10^{-5}$N bacitracin
3 mN ethylenediaminetetraacetic acid
1 mN ethyleneglycol-bis-($\beta$-aminoethyl ether)-N,N'-tetraacetic acid This buffer was kept at pH 6.8 to prevent platelet release and aggregation.

The diluted platelets were centrifuged at 2500 g and then resuspended in 50 volumes of the same buffer. The cells were then ruptured with a Branson sonicator while the suspension was maintained in an ice bath. The ruptured cells were then centrifuged at 18,000 g, resuspended in fresh buffer and recentrifuged at 18,000 g. These membranes were diluted with the above antiprotease buffer which had been adjusted to pH 7.4 and to a concentration of 3.0 mg/ml.

The test compounds were dissolved in dimethylsulfoxide at a concentration of 50 mM and then diluted 1:10 in either water, 0.1M hydrochloric acid or 0.1M sodium hydroxide. They were then diluted 1:100 in buffer to 50 μM, and 50 μl of this stock solution was placed in triplicate test tubes. The tubes were cooled to 0° C. and 200 μl of the following mixture were added:

100 μl of 3 mg/ml membrane in buffer
50 μl of 15 nM[$^3$H]imipramine in buffer
50 μl buffer The tubes were incubated for 60 minutes at 0° C. Controls contain either buffer alone (100%) of 10 μM of final desmethylimipramine (DMI) (0%).

The samples were diluted with 5 ml of buffer [0.12M-sodium chloride, 0.05M-tris buffer, 0.005M-potassium chloride (pH 7.4)], vacuum filtered and washed twice with 5 ml of buffer. Radioactivity was measured in a liquid scintillation counter and the degree of binding was calculated. The results of this test on representative compounds of this invention appear in Table III.

TABLE III

| Platelet Imipramine Binding | |
|---|---|
| Compound | % Inhibition |
| 3a(4-chlorophenyl)-2,3,3a,4,7,7a-hexahydro-4,7-methano-1H—isoindole fumarate | 98 |
| octahyro-3a-phenyl-4,7-methano-1H—isoindole fumarate | 98 |
| 2,3,3a,4,7,7a-hexahydro-2-methyl-3a-(4-methylphenyl)-4,7-methano-1H—isoindole maleate (1:1) | 98 |
| 2,3,3a,4,7,7a-hexahydro-3a-(4-methylphenyl)-4,7-methano-1H—isoindole maleate (1:1) | 94 |
| 2,3,3a,4,7,7a-hexahydro-3a-(3-methoxyphenyl)-2-methyl-4,7-methano-1H—insoindole maleate (1:1) | 86 |
| 3-(1,2,3,4,7,7a-hexahydro-2-methyl-4,7-methano-3aH—isoindol-3a-yl)phenol | 86 |
| 2,3,3a,4,7,7a-hexahydro-2-methyl-3a-[3-(trifluoromethyl)phenyl]-4,7-methano-1H—isoindole fumarate | 91 |
| 3a-(3,4-dichlorophenyl)octahydro-2-methyl-4,7-methano-1H—isoindole hydrochloride | 93 |
| 3a-(4-azidophenyl)octahydro-2,2-dimethyl-4,7-methano-1H—isoindolium iodide | 88 |
| octahydro-2-methyl-3a-(4-nitrophenyl)-4,7-methano-1H—isoindole fumarate (1:1) | 66 |
| 4-(1,2,3,4,5,6,7,7a-octahydro-2-methyl-4,7-methano-3aH—isoindol-3a-yl)benzenamine fumarate (1:1) | 80 |
| 3a-(4-chlorophenyl)octahydro-2-methyl-4,7-methano-1H—isoindole fumarate (1:1) | 91 |
| 3a-(3,4-difluorophenyl)octahydro-2-methyl-4,7-methanol-1H—isoindole fumarate (1:1) | 95 |
| 3a-(3-chlorophenyl)-2,3,3a,4,7,7a-hexahydro-2-methyl-4,7-methano-1H—isoindole fumarate (1:1) | 86 |
| 3a-(3,4-difluorophenyl)octahydro-2-methyl-4,7-ethano-1H—isoindole fumarate (1:1) | 100 |
| 3a-(3,4-dichlorophenyl)octahydro-2-methyl-4,7-ethano-1H—isoindole fumarate (1:1) | 94 |
| 3a-(3,4-dichlorophenyl)-2-ethyloctahydro-4,7-ethano-1H—isoindole fumarate (1:1) | 89 |
| 3a-(3,4-dichlorophenyl)octahydro-4,7-methano-1H—isoindole hydrochloride | 96 |

The compounds of this invention are active as antistress agents in warm-blooded animals as evidenced by their results when tested in the Stress Induced Depressed Behavior Test. In this test, rats were confined on a warm (44.5° C.), but aversive, surface for 15 minutes. After 5–6 minutes, control rats began to show episodes of depressed ("coping") behavior where they remained flat and immobile for short to long periods of time. The onset and total duration of this behavior was timed. A ratio of onset/duration was calculated. The test compounds were administered intraperitoneally at 5–20 mg/kg of body weight. Active compounds prolong the time of onset and shorten the duration time resulting in high ratios. The results of this test on representative compounds of the present invention appear in Table IV.

TABLE IV

Stress Induced Depressed Behavior Test

| Compound | Ratio onset/duration |
|---|---|
| 3a-(3,4-dichlorophenyl)octahydro-2-methyl-4,7-methano-1H—isoindole hydrochloride | 59 |
| 3a-(4-chlorophenyl)octahydro-2-methyl-4,7-methanol-1H—isoindole fumarate (1:1) | 20 |
| 3a-(3-chlorophenyl)-2,3,3a,4,7,7a-hexahydro-2-methyl-4,7-methano-1H—isoindole fumarate (1:1) | 13 |
| 3a-(3,4-dichlorophenyl)octahydro-2-methyl-4,7-ethano-1H—isoindole fumarate (1:1) | 83 |
| 3a-(3,4-dichlorophenyl)-2-ethyloctahydro-4,7-ethano-1H—isoindole fumarate (1:1) | 66 |
| 3a-(3,4-dichlorophenyl)octahydro-4,7-methano-1H—isoindole hydrochloride | 76 |

The novel compounds of the present invention possess the endo configuration at the 3a,7a-bridge and exist as the dextro-isomer, the levo-isomer, and the racemic mixture thereof. These may be represented by the following structural formula:

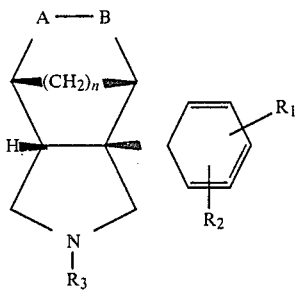

the mirror image thereof; and the racemic mixture of the two optical isomers. These racemic mixtures can be resolved by methods of resolution well known in the art. For example, the free bases can be treated with an optically active acid such as d-tartaric, l-malic, l-mandelic, d-10-camphorsulfonic or di-p-toluoyl-d-tartaric and the like to produce diastereoisomeric salts which can be separated by crystallization. Resolution of the racemic mixtures of this invention can also be accomplished by reverse phase and absorption chromatography on an optically active support and adsorbent.

The invention will be described in greater detail in conjunction with the following specific examples.

EXAMPLE 1

3-a-(4-Chlorophenyl)-2,3,3a,4,7,7a-hexahydro-4,7-methano-1H-isoindole fumarate

A 3.0 g portion of 2-p-chlorophenylmaleimide [C. S. Rondestvedt and D. Vogel, J.A.C.S., 77, 2312 (1955)] was suspended in 20 ml of dichloromethane and the slurry was cooled in an ice bath as 7.34 g of cyclopentadiene was distilled in. The mixture was stirred at room temperature for 6 hours and then poured into 150 ml of acetonitrile. The resulting solid was collected and washed with water and hexane, giving 3.02 g of 2-(p-chlorophenyl)-5-norbornene-2,3-dicarboxamide.

A mixture of 3.66 g of 2-(p-chlorophenyl)-5-norbornene-2,3-dicarboxamide in 20 ml of Vitride ®T [sodium dihydrobis(2-methoxyethoxy)aluminate (70% solution in toluene)] was stirred for 3 hours, then heated at reflux for 17 hours and cooled in an ice bath. The reaction was quenched by the slow addition of 20 ml of 10N sodium hydroxide, then was diluted with 50 ml of water and extracted with three 50 ml portions of ether. The ether extracts were combined, washed with water and brine, dried and evaporated to a yellow oil which is the free base of the desired compound.

An 830 mg portion of this oil was dissolved in 3 ml of acetone and added to a filtered solution of 423 mg of fumaric acid in 40 ml of boiling acetone, giving 0.92 g of the desired fumarate salt as a white solid, mp 226°–227.5° C.

EXAMPLE 2

Octahydro-3a-phenyl-4,7-methano-1H-isoindole fumarate

A 0.49 g portion of 3a-(4-chlorophenyl)-2,3,3a,4,7,7a-hexahydro-4,7-methano-1H-isoindole fumarate was suspended in 30 ml of ethyl acetate, washed twice with 10% sodium bicarbonate solution, dried with brine and 47 mg of 5% palladium on calcium added. The mixture was stirred under one atmosphere of hydrogen for 17 hours, then filtered, washed with 10% sodium bicarbonate, dried and evaporated, giving 0.25 g of the free base of the desired compound as a brown oil.

A 190 mg portion of this oil was converted to the fumarate salt as described in Example 1, giving 0.22 g as a white solid, mp 159°–162° C.

EXAMPLE 3

2,3,3a,4,7,7a-Hexahydro-2-methyl-3a-(4-methylphenyl)-4,7-methano-1H-isoindole maleate (1:1)

A 1.5 g portion of N-methyl-2-p-tolylmaleimide [Ger. (East) Patent 103,136] was dissolved in 20 ml of dichloromethane, cooled in an ice-salt bath. A 1.76 g portion of cyclopentadiene was distilled into the solution and the mixture was allowed to stand at room temperature overnight. The solvent was removed in vacuo giving an orange oil, which was triturated with hexane and crystallized from ethyl acetate:hexane, giving 1.32 g of N-methyl-2-p-tolyl-5-norbornene-2,3-dicarboximide.

A 1.0 g portion of the above imide was dissolved in 10 ml of toluene, 10 ml of Vitride ®T was added and the mixture was stirred for 2 hours at room temperature, then at reflux for 16 hours and then cooled. The reaction was then quenched with 5N sodium hydroxide, partitioned between ether and water, dried and evaporated to a brown oil. This oil was subjected to Kugelrohr distillation (155° C., 0.155 mm mercury), giving 0.70 g of the desired product as the free base.

A 290 mg portion of the free base was dissolved in 2 ml of ethyl acetate and added to 147 mg of maleic acid in 20 ml of boiling ethyl acetate. Cooling gave 0.36 g of the desired maleate salt as a gray solid, mp 179°–182° C.

EXAMPLE 4

3a-(3,5-Dimethoxyphenyl)-2,3,3a,4,7,7a-hexahydro-2-methyl-4,7-methano-1H-isoindole hydrochloride A 1.44 g portion of N-methyl-2-(3,4,5-trimethoxyphenyl)maleimide [P. T. Izzo, J. Org. Chem., 28, 1713 (1963)] was dissolved in 25 ml of dichloromethane in an ice-salt bath. A 1.83 g portion of cyclopentadiene was distilled into the solution and the mixture was stirred for 24 hours. The solvent was removed in vacuo and the foamy residue was triturated with hexane, taken up in hot ethyl acetate, filtered, diluted with hexane and cooled, giving 0.81 g of N-methyl-2-(3,4,5-trimethoxyphenyl)-5-norbornene-2,3-dicarboximide as a yellow solid.

A 0.6 g portion of this imide was reacted with 6 ml of Vitride®T as described in Example 3, giving 276 mg of the desired compound as the free base. The free base was converted to the hydrochloride salt by treatment with hydrochloric acid in ether.

EXAMPLE 5

2,3,3a,4,7,7a-Hexahydro-3a-(4-methylphenyl)-4,7-methano-1H-isoindole maleate (1:1)

A 53.6 g portion of p-toluidine was dissolved in a mixture of 150 ml of 12N-hydrochloric acid and 100 ml of water, cooled in an ice-salt bath. A 100 g portion of ice was added and then a solution of 35 g of sodium nitrite in 80 ml of water was added dropwise with stirring over ½ hour. A solution of 48.5 g of maleimide in 400 ml of acetone was then added in one portion and the mixture was cooled in an ice-salt bath with 20 g of dry ice added to the reaction mixture. A 125 g portion of sodium acetate was added to achieve pH 3. Ten minutes later 5.0 g of cupric chloride dihydrate was added. The mixture was filtered and the filtrate was allowed to stand 64 hours. The solid was collected, added to 30 ml of 2,6-lutidine and heated on a steam bath for ½ hour, then poured into one liter of water and filtered. The filtrate produced pale yellow crystals which were collected, giving 2-(p-tolyl)maleimide.

A 4.04 g portion of this maleimide was suspended in 30 ml of dichloromethane and 4.02 g of cyclopentadiene distilled in. After prolonged stirring the solvents were removed in vacuo and the residue digested with ethyl acetate. This solution was filtered and the filtrate subjected to preparative TLC, providing a solid which was recrystallized from ethyl acetate:ether, giving 160 mg of 2-p-tolyl-5-norbornene-2,3-dicarboxamide.

A 500 mg portion of 2-p-tolyl-5-norbornene-2,3-dicarboxamide and 5 ml of Vitride®T were reacted as described in Example 3, giving 540 mg of the desired compound in the free base state as a brown oil. This oil was taken up in 3 ml of acetone and added to 243 mg of maleic acid in 25 ml of hot acetone. The acetone was evaporated and replaced with ethyl acetate/ether, giving 250 mg of the desired maleate salt, mp 162°–165° C.

EXAMPLE 6

2,3,3a,4,7,7a-Hexahydro-3a-(3-methoxyphenyl)-4,7-methano-1H-isoindole maleate

A 61.5 g portion of m-anisidine in 150 ml of 12N hydrochloric acid and 150 ml of water was cooled in an ice-salt bath. A 35 g portion of sodium nitrite in 80 ml of water was added dropwise, with stirring over ½ hour. A solution of 48.5 g of maleimide in 400 ml of acetone was added together with 50 g of dry-ice. A 125 g portion of sodium acetate was added, followed immediately by 12.75 g of cupric chloride dihydrate. The mixture was allowed to stand 18 hours, then the solid was collected and dried. A 90 g portion of this solid and 51 g of 2,4-lutidine in 250 ml of isopropanol was heated on a steam bath for ½ hour, then poured into 1200 ml of water. The solid was collected, dried and then recrystallized, first from isopropanol then from ethyl acetate:ethanol, giving 29.0 g of 2-(m-methoxyphenyl)maleimide as yellow crystals.

A 2.19 g portion of the above maleimide was suspended in 25 ml of dichloromethane and 3.44 g of cyclopentadiene was distilled in. After standing 15 hours, the solvent was removed in vacuo and the residue was triturated with ether, taken up in hot ethyl acetate:hexane, treated with charcoal and filtered. Hexane was added to turbidity and the mixture was cooled, giving 1.60 g of 2-(m-methoxyphenyl)-5-norbornene-2,3-dicarboxamide as a yellow solid.

A 0.67 g portion of the above dicarboxamide was reacted with Vitride®T as described in Example 3, giving 0.56 g of the free base as a brown oil which was converted with 247 mg of maleic acid in 10 ml of hot ethyl acetate to give 120 mg of the desired maleate, mp 195°–197° C.

EXAMPLE 7

2,3,3a,4,7,7a-Hexahydro-3a-(3-methoxyphenyl)-2-methyl-4,7-methano-1H-isoindole maleate (1:1)

A 61.13 g portion of m-anisidine and 55.1 g of N-methylmaleimide were reacted as described in Example 6, giving 33.07 g of 2-(m-methoxyphenyl)-N-methylmaleimide.

A 10.5 g portion of the above maleimide was reacted with 23.3 g of cyclopentadiene in 100 ml of dichloromethane for 4 hours, giving 12.13 g of 2-(m-methoxyphenyl)-N-methyl-5-norbornene-2,3-dicarboxamide.

A 9.72 g portion of the above dicarboxamide and 34 ml of Vitride®T in 250 ml of toluene was reacted as described in Example 6, giving 8.76 g of the free base. A 2.0 g portion was taken up in 10 ml of hot ether and added to one gram of maleic acid in 20 ml of hot acetonitrile, giving the desired maleate salt as a brown glass.

EXAMPLE 8

3-(1,2,3,4,7,7a-Hexahydro-2-methyl-4,7-methano-3aH-isoindol-3a-yl)phenol

A 733 mg portion of sodium hydride was suspended in 25 ml of dry dimethylformamide and 1.2 ml of ethane thiol in 10 ml of dry dimethylformamide was added dropwise at ice bath temperature. A 1.92 g portion of 2,3,3a,4,7,-7a-hexahydro-3a-(3-methoxyphenyl)-2-methyl-4,7-methano-1H-isoindole was added and the solution was heated at reflux for 6 hours, then cooled and evaporated in vacuo. The residue was taken up in water, extracted with ether, then hexane and neutralized with acetic acid giving a solid which was dissolved in hot methanol and precipitated with ether, then filtered. The filtrate was partially evaporated, then precipitated with ether and hexane. Evaporation of the ether extract gave a foam which was triturated with hexane, giving 240 mg of the desired product as a brown solid, mp 129°–136° C.

EXAMPLE 9

2,3,3a,4,7,7a-Hexahydro-2-methyl-3a-[3-(trifluoromethyl)phenyl]-4,7-methano-1H-isoindole fumarate An 80.6 g portion of 3-aminobenzotrifluoride was reacted with 55.6 g of N-methylmaleimide as described in Example 6, giving 2-(m-trifluoromethylphenyl)-N-methylmaleimide.

A 3.0 g portion of this N-methylmaleimide was reacted with 13.6 g of cyclopentadiene as described in Example 6, giving 1.7 g of 2-(m-trifluoromethylphenyl)-N-methyl-5-norbornene-2,3-dicarboxamide.

A 1.0 g portion of the above dicarboxamide was reacted with Vitride®T as described in Example 6, giving 800 mg of the free base. A 328 mg portion of the free base was reacted with 151 mg of fumaric acid in hot acetone, giving 360 mg of the desired fumarate salt as white crystals, mp 158°–161° C.

EXAMPLE 10

3a-(3,4-Dichlorophenyl)octahydro-2-methyl-4,7-methano-1H-isoindole hydrochloride A 162 g portion of 3,4-dichloroaniline was reacted with 111 g of N-methylmaleimide as described in Example 6, giving 112 g of 2-(3,4-dichlorophenyl)-N-methylmaleimide.

An 18 g portion of this maleimide was reacted with 80 g of cyclopentadiene as described in Example 6, giving 12.3 g of 2-(3,4-dichlorophenyl)-N-methyl-5-norbornene-2,3-dicarboxamide.

To a 12.3 g portion of the above dicarboxamide in 250 ml of ethyl acetate was added 4 drops of concentrated hydrochloric acid and 0.8 g of platinum oxide. This mixture was hydrogenated giving 11.7 g of 2-(3,4-dichlorophenyl)-N-methyl-norbornane-2,3-dicarboxamide.

A 6.4 g portion of 2-(3,4-dichlorophenyl)-N-methyl-norbornane-2,3-dicarboxamide in 100 ml of tetrahydrofuran and 120 ml of borane-tetrahydrofuran complex was heated at reflux overnight. Careful addition of 100 ml of 6N hydrochloric acid, followed by concentration on the steam bath, basification, extraction, drying and evaporation gave 10 g of a liquid which was distilled on a Kugelrohr apparatus at 0.3 mm, giving 3.6 g of a colorless liquid and 5.3 g of distillation residue as a viscous yellow liquid, which is the free base.

This free base was dissolved in hot ethanol and acidified with ethanolic hydrochloric acid. The addition of ether produced a solid which was collected giving 3.3 g of the desired hydrochloride salt as white crystals, mp 255°–257° C.

EXAMPLE 11

4-(1,2,3,4,7,7a-Hexahydro-2-methyl-4,7-methano-3aH-isoindol-3a-yl)benzenamine fumarate (1:2)

A 100 g portion of N-methylmaleimide was reacted with 126.2 g of p-nitroaniline as described in Example 6, giving 78 g of 2-(p-nitrophenyl)-N-methylmaleimide.

A 63 g portion of the above maleimide was reacted with 50 ml of cyclopentadiene as described in Example 6, giving, upon recrystallization from ethylacetate:hexane, 17.9 g of 2-(p-nitrophenyl)-N-methyl-5-norbornene-2,3-dicarboxamide.

A 1.0 g amount of the above dicarboxamide and 3.0 g of powdered stannous chloride was suspended in 10 ml of ether and 3.3 ml of concentrated hydrochloric acid was added dropwise over 5 minutes with stirring. The resulting suspension was stirred for 16 hours at room temperature. The reaction mixture was quenched with 10 ml of 10N sodium hydroxide and the slurry was partitioned between ethyl acetate and water. After three extractions, the ethyl acetate extracts were combined, dried and evaporated in vacuo. The residue was recrystallized from ethyl acetate and gave 0.38 g of 3a-(4-aminophenyl)-3a,4,7,7a-tetrahydro-2-methyl-4,7-methano-1H-isoindol-1,3(2H)dione as a tan solid, mp 129°–131° C.

A 1.34 g amount of the preceding compound (prepared as described above) was suspended in 10 ml of toluene and 10 ml of Vitride®T was added dropwise over 5 minutes. The resulting slurry was stirred for 16 hours at room temperature, then at reflux for 1½ hours. The cooled reaction mixture was then quenched with 12 ml of 5N sodium hydroxide, poured into 50 ml of water and extracted with three-50 ml portions of ethyl acetate. Drying and evaporation in vacuo gave 1.17 g of a dark oil. Kugelrohr distillation (160° C./0.02 mm mercury) gave 1.02 g of the free base as a pale yellow oil.

A 0.8 g portion of this free base was reacted with 0.8 g of fumaric acid in 80 ml of boiling acetone giving 0.70 g of the desired fumarate salt as a glassy solid, mp 55°–56° C.

EXAMPLE 12

3a-(4-Azidophenyl)octahydro-2-methyl-4,7-methano-1H-isoindole

A 200 mg portion of 4-(1,2,3,4,7,7a-hexahydro-2-methyl-4,7-methano-3aH-isoindol-3a-yl)benzenamine was suspended in 35 ml of water, the pH was adjusted to 1.6 and the solution was cooled to 5° C. A 59 mg portion of sodium nitrite was added and the mixture was stirred for one hour at 5° C. A 54 mg portion of sodium azide was added, the cooling bath removed and the reaction protected from light for one hour. Still protected from light, the mixture was diluted with ether, made basic with sodium hydroxide and evaporated at reduced pressure, giving 210 mg of the desired product as a brown oil.

EXAMPLE 13

3a-(4-Azidophenyl)octahydro-2,2-dimethyl-4,7-methano-1H-isoindolium iodide

A mixture of 150 mg of 3a-(4-azidophenyl)octahydro-2-methyl-4,7-methano-1H-isoindole and 0.05 ml of methyl iodide in 4 ml of ether was allowed to stand for 2 weeks to give 200 mg of the desired product as a yellow solid.

EXAMPLE 14

Octahydro-2-methyl-3a-(4-nitrophenyl)-4,7-methano-1H-isoindole fumarate (1:1)

A 126.2 g (0.91 mole) amount of p-nitroaniline was suspended in 275 ml of concentrated hydrochloric acid and 370 ml of water. The slurry was cooled in an ice-salt bath and a 62.9 g (0.91 mole) portion of sodium nitrite in 150 ml of water was added. The resulting slurry was stirred at about 5° C. for one hour. A solution of 100 g (0.90 mole) of N-methyl maleimide in 600 ml of acetone was added together with 650 g of ice, then 23.0 g of cupric chloride dihydrate was added and the slurry was stirred for 16 hours. The mixture was filtered and the wet cake suspended in 1.5 liter of isopropanol, then 106 ml of 2,6-lutidine was added and the mixture was heated to boiling. The green slurry was poured into 4 liter of water, cooled and filtered to give 163 g of a yellow solid which was recrystallized from 1400 ml of acetone, giving 78.0 g of N-methyl-2-(p-nitrophenyl)maleimide as a yellow solid, mp 163°–165.5° C.

A 63.0 g portion of this maleimide was dissolved in 350 ml of dichloromethane and 50 ml of cyclopentadiene was distilled in. After prolonged stirring the solvents were removed in vacuo and the residue was subjected to preparative liquid chromatography to provide 43.6 g of a crude product. This material was recrystallized from ethyl acetate:hexane. The product was collected by filtration (the filtrate was set aside) and gave 17.9 g of N-methyl-2-(p-nitrophenyl)-5-norbornene-2,3-dicarboxamide as a brown solid, mp 164°–166° C.

A 1.5 g amount of the above dicarboximide was dissolved in 30 ml of toluene:ethanol (3:2), with warming. The resulting solution was cooled, then 150 mg of chlorotris(triphenylphosphine)rhodium (Wilkinsons catalyst) was added and the mixture was shaken on a Parr apparatus for one hour at a pressure of 35 psi. The solid precipitate was collected by filtration and after preparative liquid chromatography gave 1.54 g of a mixture. The above described procedure was repeated with the mixture using 50 ml of toluene:ethanol (3:1), 100 mg of Wilkinsons catalyst for a period of 4 hours at 42 psi. The reaction mixture was then cooled and filtered and gave 0.90 g of residue. The residue was subjected to conventional high pressure liquid chromatography and gave 0.60 g of 3a,4,7,7a-tetrahydro-2-methyl-3a-(4-nitrophenyl)-4,7-methano-1H-isoindole-1,3(2H)-dione as a yellow solid, mp 163°–167° C.

A mixture of 0.56 g of the above dione and 11.0 ml of borane (1M borane-tetrahydrofuran complex) were heated at reflux for 18 hours. The cooled reaction mixture was quenched with 15 ml of 3N sulfuric acid and heated on a steam bath for 16 hours. The solution was cooled, extracted once with ether and made basic with sodium hydroxide. Work-up with ether gave 0.46 g of a red oil that was subjected to Kugelrohr distillation and gave 0.41 g of the free base as a red liquid.

A 0.25 g portion of the red liquid was added to a boiling solution of 116 mg of fumaric acid in 10 ml of acetone giving 0.31 g of the desired fumarate salt, mp 174°–177° C.

EXAMPLE 15

4-(1,2,3,4,5,6,7,7a-Octahydro-2-methyl-4,7-methano-3aH-isoindol-3a-yl)benzenamine fumarate (1:1)

The ethyl acetate:hexane filtrate remaining from the recrystallization step for N-methyl-2-(p-nitrophenyl)-5-norbornene-2,3-dicarboximide described in Example 14 was separated into 2 batches which were hydrogenated in a Parr shaker with 2½ teaspoons of Raney nickel catalyst and shaken for 16 hours to give a total of 24.9 g of a yellow red foam. The residue from the first batch was taken up in 200 ml of isopropanol, treated with activated charcoal, cooled and filtered. The filtrate was hydrogenated for 48 hours on a Parr shaker using 500 mg of 5% palladium catalyst on carbon. The solution was filtered and evaporated and gave a red gummy foam. The hydrogenation step was repeated on this material using palladium catalyst on carbon in acetic acid for 16 hours. The reaction mixture was filtered and evaporated in vacuo. The residue was partitioned between ethyl acetate/sodium bicarbonate solution. The organic layer was dried over anhydrous sodium sulfate and evaporated in vacuo to give 4.3 g of a red foam. The foam was subjected to preparative high pressure liquid chromatography to separate the crude product. This material was recrystallized from ethyl acetate and water to give 1.37 g of 3a-(4-aminophenyl)hexahydro-2-methyl-4,7-methano-1H-isoindole-1,3(2H)-dione as a pink solid, mp 131°–133° C.

A 1.10 g amount of the above dione was suspended in 10 ml of toluene and 8.0 ml of Vitride®T was added dropwise over 5 minutes. The resulting slurry was stirred for 16 hours at room temperature, then at reflux for 1.5 hours. The reaction mixture was cooled, then quenched with 12 ml of 5N sodium hydroxide. The resulting mixture was poured into 50 ml of water and extracted with three 50 ml portions of ethylacetate. Drying and evaporation gave 1.15 g of a brown oil. The oil was distilled on a Kugelrohr apparatus at 120° C./0.05 mm to give the free base as a colorless liquid.

A 0.76 g amount of the free base was dissolved in 5 ml of acetone and added to a boiling solution of 0.76 g of fumaric acid in 65 ml of acetone with formation of a gum. The supernatant was decanted and the gum was dried in vacuo giving 0.43 g of the desired fumarate salt as a yellow solid, mp 71°–76° C.

EXAMPLE 16

3a-(4-Chlorophenyl)octahydro-2-methyl-4,7-methano-1H-isoindole fumarate (1:1)

A 5.1 g amount of N-methyl-2-(p-nitrophenyl)-5-norbornene-2,3-dicarboximide (prepared in Example 14) was reduced in a Parr shaker with 150 ml of ethyl acetate, 400 mg of 5% palladium catalyst on carbon and 3 ml of acetic acid. The reaction mixture was filtered and the catalyst washed with ethanol. The filtrate was evaporated in vacuo giving 5.54 g of a gum which solidified when triturated with ether. The solid was dissolved in 50 ml of toluene and 35 ml of Vitride®T was added dropwise over ½ hour. The resulting slurry was stirred at room temperature for 16 hours, then refluxed for 3 hours. The reaction was quenched with 55 ml of 5N sodium hydroxide and partitioned between ethyl acetate and water. The resulting brown oil was distilled on a Kugelrohr apparatus at 150° C./0.2 mm, giving 3.60 g of 4-(1,2,3,4,5,6,7,7a-octahydro-2-methyl-4,7-methano-3aH-isoindol-3a-yl)benzenamine as a pale yellow oil.

A 750 mg amount of the preceding material was suspended in 35 ml of water. The pH of the suspension was adjusted to pH 1.6 with hydrochloric acid and the solution was cooled to 5° C. A 225 mg portion of sodium nitrite was added and the solution was stirred at 5° C. for one hour. A 350 mg amount of cuprous chloride was dissolved in 4 ml of concentrated hydrochloric acid and this solution was added to the reaction mixture. The cooling bath was removed and the mixture was stirred for 16 hours. The solution was made basic with ammonium hydroxide and extracted with ether. The extracts were dried and evaporated in vacuo giving a black oil. Kugelrohr distillaton gave 0.49 g of the free base as a yellow oil.

A 0.39 g portion of this free base was reacted with 184 mg of fumaric acid in 10 ml of boiling acetone, giving 0.49 g of the desired fumarate salt as a yellow solid, mp 159°–162° C.

EXAMPLE 17

3a-(3,4-Difluorophenyl)octahydro-2-methyl-4,7-methano-1H-isoindole fumarate (1:1)

A 25 g amount of 3,4-difluoroaniline was dissolved in 275 ml of water and 57 ml of concentrated hydrochloric acid. The solution was cooled to 5° C. in a cooling bath and a solution of 13.1 g of sodium nitrite in 25 ml of water was added dropwise to the reaction mixture over a 25 minute period. A solution of 22.0 g of N-methyl maleimide and 4.8 g of cupric chloride dissolved in 200 ml of warm acetone was then added to the reaction mixture at 0° C. over a 20 minute period with stirring. Stirring was continued for one hour until the evolution of gas ceased. The reaction mixture was warmed to 10° C. and the pH adjusted to and maintained at pH 3.0 with sodium bicarbonate and hydrochloric acid. After standing at room temperature for 16 hours, the mixture was filtered to collect the product. The product was heated to boiling in 250 ml of isopropanol containing 22 ml of 2,6-lutidine. The boiling solution was poured into one liter of water, filtered, dried and recrystallized from acetone giving 14.9 g of 3-(3,4-difluorophenyl)-1-methyl-1H-pyrrole-2,5-dione as a yellow solid, mp 121°–123° C.

Dicyclopentadiene was heated in an oil bath and the cyclopentadiene which formed was distilled and collected in a cooled receiver in an ice bath containing a solution of 18.1 g of the above dione in 150 ml of dichloromethane and sufficient acetone to insure solution on cooling. The reaction mixture was stirred at room temperature for 16 hours, the solvent was removed in vacuo and the dark residue was recrystallized from acetonitrile:water to give 10.24 g of 3a-(3,4-difluorophenyl)-3a,4,7,7a-tetrahydro-2-methyl-4,7-methano-1H-isoindole-1,3(2H)-dione as a white solid, mp 116°–120° C.

To an 8.5 g portion of the preceding compound in 150 ml of ethyl acetate was added 3 drops of concentrated hydrochloric acid and 0.5 g of platinum oxide. This mixture was hydrogenated on a Parr apparatus and filtered. The filter was washed with hot methanol and the filtrate was evaporated in vacuo to give a white solid. The solid was recrystallized from ethyl acetate:hexane and gave 7.43 g of 3a-(3,4-difluorophenyl)hexahydro-2-methyl-4,7-methano-1H-isoindol-1,3(2H)-dione as a tan solid, mp 96°–100° C.

A 4.0 g portion of the preceding compound was dissolved in 25 ml of tetrahydrofuran and 80 ml of borane (1M borane-tetrahydrofuran complex) was added dropwise. The solution was stirred at room temperature for 16 hours and at reflux for 6 hours. The cooled reaction mixture was quenched with 50 ml of 6N hydrochloric acid and heated on a steam bath. The solution was made basic with ammonium hydroxide and extracted with dichloromethane giving a greenish oil after solvent evaporation. The oil was redissolved in dichloromethane and heated at reflux for 16 hours. Evaporation in vacuo gave 3.34 g of crude product. Kugelrohr distillation at 130° C./0.1 mm gave 2.10 g of 3a-(3,4-difluorophenyl)octahydro-2-methyl-4,7-methano-1H-isoindole as a yellowish oil.

A 1.99 g portion of this oil was reacted with 0.90 g of fumaric acid in hot acetone giving the desired fumarate salt as a white solid, mp 173°–175° C.

EXAMPLE 8

3a-(3-Chlorophenyl)2,3,3a,4,7,7a-hexahydro-2-methyl-4,7-methano-1H-isoindole fumarate (1:1)

To a 127.6 g amount of 3-chloroaniline dissolved in a mixture of 400 ml of water and 300 ml of 12N hydrochloric acid, cooled in an ice-salt bath was added dropwise over a 60 minute period a solution of 69 g of sodium nitrite in 100 ml of water, maintaining the solution temperature below 15° C. A solution of 111 g of N-methylmaleimide and 25 g of cupric chloride dihydrate in one liter of acetone was added slowly to the stirred reaction mixture over a one hour period maintaining the temperature of the mixture at <20° C. during the addition. Then sodium bicarbonate was added cautiously to adjust the pH to 2.8. The supernatant liquid was decanted and the residual brown tar was partially dissolved in 1.4 liters of isopropanol and filtered. The filtrate was mixed with 107 g of 2,6-lutidine and heated on a steam bath for one hour. This solution was poured into 2 liters of water with formation of a precipitate. After standing at room temperature for 16 hours the mixture was filtered to collect 187 g of a brown solid. The solid was recrystallized from isopropanol and gave 88.3 g of light brown crystals. The filtrate was concentrated in vacuo and gave a tacky brown solid. This solid was recrystallized from 900 ml of ethanol and gave 32.0 g of 2-(m-chlorophenyl)-N-methylmaleimide as straw colored crystals, mp 111°–113° C.

A 5.0 g portion of the preceding maleimide was dissolved in 50 ml of dichloromethane. Then cyclopentadiene was distilled in as described in Example 17. The reaction mixture was stirred at room temperature for 16 hours. The solvents were removed in vacuo and the residue was chromatographed on a Waters Prep 500A Liquid Chromatograph using a silica gel column and eluting with hexane:ethyl acetate (70:30) giving 3.55 g of a red gum. The gum was recrystallized from diisopropyl ether:hexane and gave 2.44 g of 3a-(3-chlorophenyl)-3a,4,7,7a-tetrahydro-2-methyl-4,7-methano-1H-isoindol-1,3(2H)-dione as a tan solid, mp 98°–100° C.

A 2.0 g portion of the above dione was reacted with 5 ml of Vitride ®T as described in Example 15 to yield a brown oil which was subjected to Kugelrohr distillation (130° C., 0.05 mm mercury), giving 0.88 g of a pale yellow oil as the free base product.

A 760 mg portion of the free base oil was added to a boiling solution of 340 mg of fumaric acid in 35 ml of acetone, giving 0.94 g of the desired fumarate salt as a white solid, mp 163.5°–165° C.

EXAMPLE 19

3a-(1,3-Benzodioxol-5-yl)-2,3,3a,4,7,7a-hexahydro-2-methyl-4,7-methano-1H-isoindole fumarate (1:1)

A 30.9 g amount of 3,4-methylenedioxyaniline hydrochloride was dissolved in 90 ml of water and 40 ml of concentrated hydrochloric acid. The solution was cooled to 5° C. in an ice-salt bath and a solution of 12.3 g of sodium nitrite in 35 ml of water was added dropwise to the reaction mixture over a 25 minute period. A solution of 20.0 g of N-methylmaleimide and 2.4 g of cupric chloride in 150 ml of acetone was added to the reaction mixture portionwise with stirring. The reaction mixture temperature was maintained at 3° C. and the pH was adjusted to 3.2 by the addition of about 30 g of sodium bicarbonate. After standing at room temperature for 16 hours the mixture was filtered to collect a black solid. The solid was dried. Then the solid was dissolved in 500 ml of isopropanol containing 19.5 g of 2,6-lutidine. The mixture was heated to boiling and filtered hot to collect 4.8 g of isoluble material. The filtrate was cooled and an additional 2.6 g of precipitate was collected. This filtrate was reduced in volume to 200 ml and cooled and filtered to collect 2.7 g more of precipitate. The final filtrate was diluted with water and filtered to collect 0.9 g of additional material. The precipitates were combined and subjected to preparative liquid chromatography using a silica gel column and ethyl acetate:hexane (1:1) as eluent. The second cut, 0.6 g was recrystallized from ethyl acetate to give 0.1 g of 3-(1,3-benzodioxol-5-yl)-1-methyl-1H-pyrrole-2,5-dione as a brown solid, mp 210°–215° C.

The entire amount of the preceding dione, 0.1 g, was dissolved in 5.0 ml of dichloromethane. Then cyclopentadiene was distilled in as described in Example 17. The reaction mixture was stirred at room temperature for 16 hours and subjected to preparative liquid chromatography to obtain 20 mg of an oil. The oil was triturated with diethyl ether and gave 3a-(1,3-benzodioxol-5-yl)-

3a,4,7,7a-tetrahydro-2-methyl-4,7-methano-1H-isoindol-1,3(2H)-dione as a yellow solid, mp 115.5°–118° C.

The preceding product, <20 mg, was dissolved in 3.0 ml of toluene, 1.0 ml of Vitride®T was added and the mixture was stirred for 2 hours at room temperature, then at 80° C. for 16 hours. The cooled reaction mixture was quenched with 5N sodium hydroxide, partitioned between ether and water, dried and evaporated to an oil. This oil was subjected to Kugelrohr distillation (170° C./90µ mercury) giving 22 mg of 3a-(1,3-benzodioxol-5-yl)-2,3,3a,4,7,7a-hexahydro-2-methyl-4,7-methano-1H-isoindole as a colorless liquid.

The free base oil was dissolved in 2 ml of acetone and 10 mg of fumaric acid was added. The volume was reduced to ½ ml and cooled giving 30 mg of the desired fumarate salt as a gum.

EXAMPLE 20

Octahydro-2-methyl-3a-(5,6,7,8-tetrahydro-2-naphthalenyl)-4,7-methano-1H-isoindole fumarate (1:1)

A 19.5 g amount of 5,6,7,8-tetrahydro-2-naphthalenamine [W. Davis, J. L. Everett and C. J. Ross, J.C.S., Part II, 270, 1331 (1950)] in 50 ml of water and 36 ml of 12N hydrochloric acid was stirred and cooled in an ice-salt bath. A solution of 9.0 g of sodium nitrite in 50 ml of water was added dropwise, with stirring, over a 20 minute period maintaining the reaction mixture temperature at <12° C. A solution of 14.4 g of N-methyl maleimide and 3.3 g of cupric chloride dihydrate in 70 ml of acetone was then added slowly, during 30 minutes, maintaining the temperature below 10° C. during the addition. The pH was adjusted to pH 3.0 by the slow addition of sodium bicarbonate and the mixture was allowed to stand for 60 hours at room temperature.

The solvent was decanted to leave a tacky, gummy, solid residue. The residue was mixed with 500 ml of isopropanol and 13.9 g of 2,6-lutidine and was heated on a steam bath for one hour. This mixture was diluted with 600 ml of water and allowed to stand for 16 hours. The precipitate formed was collected by filtration, dissolved in hot ethanol, treated with activated charcoal and filtered. The filtrate was allowed to stand with crystallization of the product. Filtration gave 5.2 g of 1-methyl-3-(5,6,7,8-tetrahydro-2-naphthalenyl)-1H-pyrrole-2,5-dione as brown crystals, mp 104°–107° C.

A 4.6 g portion of the preceding compound was dissolved in dichloromethane. The solution was cooled in an ice bath and 58 g of cycopentadiene was distilled in as described in Example 17. The brown reaction mixture was stirred at room temperature for 16 hours, then was concentrated in vacuo to provide a brown tar. This material was dissolved in hot ethyl acetate. Hexane was added and the slight precipitate formed was removed by filtration. The filtrate was concentrated in vacuo and the brown residue was chromatographed on a Waters Prep 500A LC using a silica gel column and eluting with 10% ethyl acetate/hexane and gave 3.1 g of a viscous liquid. On standing with scratching the liquid solidified giving the compound 3a,4,7,7a-tetrahydro-2-methyl-3a-(5,6,7,8-tetrahydro-2-naphthalenyl)-4,7-methano-1H-isoindole-1,3(2H)-dione as a brown solid, mp 78°–86° C.

To a 1.5 g portion of the above dicarboxamide in 100 ml of ethyl acetate was added 150 mg of platinum oxide and 2 drops of concentrated hydrochloric acid. This mixture was hydrogenated in a Parr apparatus for 4 hours. The reaction mixture was filtered and the filtrate was concentrated in vacuo giving 1.4 g of a viscous liquid. The liquid was crystallized with scratching giving the compound hexahydro-2-methyl-3a-(5,6,7,8-tetrahydro-2-naphthalenyl)-4,7-methano-1H-isoindol-1,3(2H)-dione as straw colored crystals, mp 108°–114° C.

To a stirred solution of 1.0 g of the preceding product in 25 ml of toluene was added, dropwise, under nitrogen, at room temperature, 20 ml of Vitride®T and 20 ml of toluene. This solution was heated at reflux under nitrogen for 16 hours, then cooled in an ice bath. The excess hydride was decomposed by the cautious addition of 10N sodium hydroxide. The mixture was diluted with water and the organic layer was separated. The aqueous phase was extracted with dichloromethane and the extract was combined with the toluene layer and dried over anhydrous sodium sulfate. This solution was concentrated in vacuo and gave a viscous light brown liquid. Kugelrohr distillation at 0.3 mm gave 0.9 g of octahydro-2-methyl-3a-(5,6,7,8-tetrahydro-2-naphthalenyl)-4,7-methano-1H-isoindole as a viscous, colorless liquid, bp 140°–150° C.

A 0.3 g sample of the above free base was reacted with 0.124 g of fumaric acid in hot acetone giving 0.38 g of the desired fumarate salt as white crystals, mp 165°–168° C.

EXAMPLE 21

3a-(3,4-Difluorophenyl)octahydro-2-methyl-4,7-ethano-1H-isoindole fumarate (1:1)

A 5.0 g amount of 3-(3,4-difluorophenyl)-1-methyl-1H-pyrrole-2,5-dione was dissolved in 25 ml of chloroform with warming. The solution was cooled to room temperature and 2.0 g of cyclohexadiene was added. After prolonged standing another 1½ ml of diene was added with a small amount of butylated hydroxytoluene. The solution was heated at reflux for 24 hours. The reaction mixture was subjected to high pressure liquid chromatography using a silica gel column and 20% ethyl acetate in hexane as eluent giving 4.9 g of 3a-(3,4-difluorophenyl)-3a,4,7,7a-tetrahydro-2-methyl-4,7-ethano-1H-isoindole-1,3(2H)-dione as a white solid, mp 125°–127° C.

To a 4.7 g amount of the preceding compound in 75 ml of ethyl acetate was added 2 drops of concentrated hydrochloric acid and 0.25 g of platinum oxide. This mixture was hydrogenated for 45 minutes on a Parr apparatus, then filtered through diatomaceous earth. The filtrate was dried over anhydrous sodium sulfate, then evaporated in vacuo giving 4.3 g of 3a-(3,4-difluorophenyl)hexahydro-2methyl-4,7-ethano-1H-isoindol-1,3(2H)-dione as a white solid, mp 133°–136° C.

An 80 ml amount of 1M borane-tetrahydrofuran complex was added dropwise to 4.1 g of the above solid product. The resulting solution was heated at reflux for 15 hours. The cooled reaction mixture was quenched with 70 ml of 4N sulfuric acid and stirred at room temperature for several days. The homogeneous solution was heated on a steam bath for 16 hours, cooled and extracted once with diethyl ether. The aqueous solution was made basic with sodium hydroxide and extracted with dichloromethane. Drying and evaporation in vacuo gave a yellow oil. Kugelrohr distillation at 150° C./0.15 mm gave 2.72 g of the desired free base as a colorless oil.

A 2.45 g portion of the free base was added to a boiling solution of 1.10 g of fumaric acid in 75 ml of acetone, giving 3.32 g of the desired fumarate salt as a white solid, mp 193°–195° C.

EXAMPLE 22

3a-(3,4-Dichlorophenyl)octahydro-2-methyl-4,7-ethano-1H-isoindole fumarate (1:1)

A stirred mixture of 10.2 g of 2-(3,4-dichlorophenyl)-N-methylmaleimide, 12.8 g of 1,3-cyclohexadiene, 0.5 g of hydroquinone and 400 ml of chloroform was heated under reflux for 48 hours. The reaction solution was concentrated in vacuo to give a viscous brown liquid which crystallized to a tan solid. The solid was dissolved in hot chloroform and filtered. The filtrate was cooled and filtered to remove some crystals. Hexane was added to the final filtrate and 2.5 g of crystals (A) were collected by filtration. The filtrate was concentrated and gave 10 g of a tacky brown solid (B). The crystals (A) and the solid (B) were combined and chromotographed by high pressure liquid chromatography on a silica gel column, eluting with 10% ethyl acetate in hexane and gave 9.8 g of 3a-(3,4-dichlorophenyl)-3a,4,7,7a-tetrahydro-2-methyl-4,7-ethano-1H-isoindole-1,3(2H)-dione as straw colored crystals, mp 125°–128° C.

A mixture of 8.0 g of the above dicarboximide, 0.8 g of platinum oxide and 3 drops of concentrated hydrochloric acid in 150 ml of ethyl acetate was hydrogenated in a Parr apparatus. The reaction mixture was filtered and the filtrate was concentrated in vacuo giving 7.4 g of 3a-(3,4-dichlorophenyl)hexahydro-2-methyl-4,7-ethano-1H-isoindole-1,3(2H)-dione as straw colored crystals, mp 126°–134° C.

To a solution of 3.4 g of the preceding compound in tetrahydrofuran was added dropwise, at room temperature, over a 15 minute period, under nitrogen, 60 ml of 1M borane-tetrahydrofuran complex. The reaction mixture was heated under reflux for 16 hours. The mixture was cooled, quenched with 25 ml of 6N sulfuric acid and concentrated under nitrogen on a steam bath. The concentrate was diluted with water and heated on the steam bath for 8 hours then cooled. The suspended solid was filtered off and the filtrate was washed with diethyl ether. The aqueous layer was made basic with sodium hydroxide pellets and extracted with dichloromethane. The extracts were dried and concentrated and gave a viscous liquid. Kugelrohr distillation at 0.7 mm gave 0.35 g of the desired free base as a viscous colorless liquid, bp 150°–155° C.

A 0.26 portion of this free base was reacted with 0.130 g of fumaric acid in boiling acetone giving 0.114 g of the desired fumarate salt as white crystals, mp 187°–189° C.

EXAMPLE 23

3a-(3,4-Dichlorophenyl)-2-ethyloctahydro-4,7-ethano-1H-isoindole fumarate (1:1)

A 260 g portion of 3,4-dichloroaniline was dissolved in a mixture of 400 ml of concentrated hydrochloric acid and 1.5 liters of water, cooled to 15° C. in an ice-salt bath. A solution of 111 g of sodium nitrite in 250 ml of water was added dropwise, with stirring, over a 90 minute period. Then 40 g of cupric chloride dihydrate was added followed by 200 g of N-ethylmaleimide in one liter of warm acetone. The reaction mixture was cooled to 10° C. and sodium bicarbonate was added in portions over 2 hours to adjust the pH to 3.5. The mixture was allowed to stand for 48 hours. The precipitate formed was collected, air dried, and taken up in 2.5 liters of isopropanol, then 185 ml of 2,6-lutidine was added and the mixture was heated to boiling, then poured into water and allowed to stand. The solid was collected and dried. Recrystallization from acetone gave 187.1 g of 3-(3,4-dichlorophenyl)-1-ethyl-1H-pyrrole-2,5-dione as a yellow solid, mp 138°–141° C.

A solution of 7.5 g of the above maleimide, 2.25 g of 1,3-cyclohexadiene, and 10 mg of methylene blue in 25 ml of dichloromethane was heated at reflux for 5 hours, then an additional one ml of the diene was added and the solution was heated for 24 hours. The cooled reaction mixture was subjected to high pressure liquid chromatography on a silica gel column eluting with hexane:ethyl acetate (4:1) and gave 5.58 g of 3a-(3,4-dichlorophenyl)-2-ethyl-3a,4,7,7a-tetrahydro-4,7-ethano-1H-isoindol-1,3(2H)-dione as a white solid, mp 122°–126° C.

A solution of 5.0 g of the preceding imide in 125 ml of ethyl acetate with 3 drops of glacial acetic acid and 0.25 g of platinum oxide was shaken for 16 hours in a Parr apparatus under 48 psi of hydrogen. The mixture was filtered through diatomaceous earth and the filtrate was evaporated in vacuo. The residue was recrystallized from ethyl acetate/hexane and gave 4.74 g of 3a-(3,4-dichlorophenyl)-2-ethylhexahydro-4,7-ethano-1H-isoindol-1,3(2H)-dione as a white solid, mp 131°–134° C.

A mixture of 4.12 g of the above compound in 15 ml of tetrahydrofuran, 65 ml of 1M borane in tetrahydrofuran and an additional 120 ml of tetrahydrofuran was stirred at room temperature for 16 hours and then heated at reflux for 8 hours. The reaction mixture was cooled, an additional 30 ml of 1M borane-tetrahydrofuran solution was added, and the mixture was heated at reflux for an additional 10 hours. The cooled reaction mixture was quenched with 90 ml of 4N sulfuric acid and the resulting mixture was heated on a steam bath for 3 hours. The residue was diluted with 260 ml of water and worked with 100 ml of ethyl acetate. The aqueous phase was made basic with sodium hydroxide and extracted with three 100 ml portions of ether. The combined ethereal extracts were washed with brine, dried over anhydrous sodium sulfate and evaporated in vacuo giving an oil. Kugelrohr distillation at 160° C., 0.2 mm mercury, gave 2.12 g of the desired free base as a pale yellow oil.

A 1.74 g portion of the free base was added to a boiling solution of 700 mg of fumaric acid in 45 ml of acetone. Cooling gave 2.3 g of the desired fumarate salt as a white solid, mp 187.5°–189.5° C.

EXAMPLE 24

3a-(3-Bromophenyl)octahydro-2-methyl-4,7-methano-1H-isoindole hydrochloride

An 86 g portion of m-bromoaniline was dissolved in a mixture of 150 ml of 12N hydrochloric acid and 100 ml of water, cooled in an ice-salt bath. A 100 g portion of ice was added, followed by a solution of 34.5 g of sodium nitrite in 80 ml of water, added dropwise over 45 minutes. A solution of 55.5 g of N-methylmaleimide and 12.5 g of cupric chloride dihydrate in 700 ml of acetone was then added slowly over 40 minutes, while maintaining the temperature between 10° C. and 15° C. A 56 g portion of sodium bicarbonate was added to achieve pH 2.6. The mixture was allowed to stand for 72 hours, and the resultant oil was extracted with 300 ml of chloroform. This solution was filtered through magnesium silicate. The filtrate was evaporated in vacuo and gave a crude crystalline product. The crude product was combined with 58 ml of 2,6-lutidine and 600 ml of isopropyl alcohol and heated on a steam bath for ½ hour. The reaction mixture was poured into 1.25 liters of water and allowed to stand at room temperature for 18 hours. The crystalline product was collected, washed with water, air dried, and then recrystallized from 500 ml of acetonitrile to give 62.5 g of 2-(m-bromophenyl)-N-methylmaleimide.

A 59.5 g portion of this maleimide was suspended in 750 ml of dichloromethane and 200 g of cyclopentadiene was distilled into the solution. After prolonged stirring, the solvents were removed in vacuo and the residue was digested with ethyl acetate to give 50 g of 2-m-bromophenyl-1-methyl-5-norbornene-2,3-dicarboxamide, as white crystals, mp 111°–113° C.

A portion of the preceding compound was hydrogenated as described in Example 10 to give 3a-(3-bromophenyl)hexahydro-2-methyl-4,7-methano-1H-isoindole-1,3-(2H)dione, mp 105°–107° C. A portion of the preceding dicarboximide in tetrahydrofuran was reacted with borane-tetrahydrofuran complex, and this solution was heated at reflux. The solvent was removed in vacuo, and the residue was heated with ethanolic hydrogen chloride to give the title compound as the hydrochloride, mp 204°–206° C.

EXAMPLE 25

3a-(3,4-Dichlorophenyl)octahydro-2-methyl-4,7-propano-1H-isoindole hydrochloride A mixture of 0.7 g (0.0027 mole) of 2-(3,4-dichlorophenyl-N-methylmaleimide and 5.0 g (0.05 mole) of 1,3-cycloheptadiene in a pressure vessel was heated in an oil bath at a bath temperature of 180° C. for 24 hours. The reaction vessel was cooled to room temperature and the contents were dissolved in and removed with the aid of dichloromethane and acetone. The solution was concentrated in vacuo and gave a tacky glass. The glass was dissolved in dichloromethane and filtered through hydrous magnesium silicate. The filtrate was again concentrated in vacuo and gave a glass. The glass was dissolved in dichloromethane and was chromatographed on a Waters Prep 500A LC, using a silica gel column and eluting with 10% ethyl acetate/hexane and gave 0.56 g of 3a-(3,4-dichlorophenyl)-3a,4,7,7a-tetrahydro-2-methyl-4,7-propano-1H-isoindol-1,3(2H)-dione as a yellow glass, mp 110°–115° C., mass spectrum, m/e 349.

A portion of the above dione is hydrogenated as described in Example 10 to give the compound 3a-(3,4-dichlorophenyl)hexahydro-2-methyl-4,7-propano-1H-isoindole-1,3(2H)-dione.

A portion of the above compound in tetrahydrofuran and borane-tetrahydrofuran complex is heated at reflux and the procedure of Example 10 is continued giving the desired free base. The free base is dissolved in hot ethanol and acidified with ethanolic hydrochloric acid. The addition of ether produces a solid which is collected, giving the desired hydrochloride salt.

EXAMPLE 26

3a-(3,4-Dichlorophenyl)octahydro-4,7-methano-1H-isoindole hydrochloride

To a solution of 5.0 g of 3a-(3,4-dichlorophenyl)octahydro-2-methyl-4,7-methano-1H-isoindole in 200 ml of toluene was added, dropwise over a 30 minute period, at room temperature, 30 ml of a solution of freshly distilled ethyl chloroformate in toluene. The reaction mixture was heated under reflux for 16 hours, then was concentrated in vacuo to give a colorless, viscous liquid. This liquid was dissolved in dichloromethane and chromatographed by preparative liquid chromatography on a silica gel column, eluting with 10% ethyl acetate/hexane and gave 1.9 g of 3a-(3,4-dichlorophenyl)octahydro-4,7-methano-2H-isoindole-2-carboxylic acid, ethyl ester as a slightly yellow, viscous liquid.

A stirred mixture of 1.6 g of the preceding compound and 30 ml of 48% hydrobromic acid was heated under reflux for 3 hours. After cooling, the mixture was filtered to collect 1.1 g of gray crystals. The crystals were recrystallized from ethanol/hexane to give 0.8 g of 3a-(3,4-dichlorophenyl)octahydro-4,7-methano-1H-isoindole hydrobromide as gray crystals, mp 260°–265° C. (dec.).

An 0.8 g amount of the above hydrobromide was dissolved in 250 ml of hot water, then filtered. The filtrate was made basic with 10N sodium hydroxide and extracted with both dichloromethane and ether. The combined organic solutions were dried over anhydrous sodium sulfate and evaporated in vacuo to give 0.35 g of a viscous liquid. This liquid was dissolved in ether and acidified with anhydrous hydrogen chloride to form a solid. The solid was collected and recrystallized from ethanol hexane to give 0.11 g of the product of the Example as gray crystals, mp 246°–248° C. (dec.).

EXAMPLE 27

(+)-3a-(3,4-Dichlorophenyl)octahydro-2-methyl-4,7-methano-1H-isoindole hydrochloride A 0.653 g portion of 3a-(3,4-dichlorophenyl)octahydro-2-methyl-4,7-methano-1H-isoindole in 25 ml of ethyl acetate was combined with 0.773 g of di-p-toluoyl-d-tartaric acid in 25 ml of ethyl acetate. The crystals that formed were collected by filtration to give 0.747 g of the (1:1) salt. This salt was dissolved in water and the solution made basic with sodium hydroxide. The oil which precipitated was extracted with ether. The ether extract yielded 0.297 g of amine which was dissolved in ether and the solution saturated with hydrogen chloride gas. Filtration yielded 0.276 g of the desired (+) product as colorless crystals, mp 250°–253° C., $[\alpha]_D^{26} +4°$ (C=0.8%, water).

EXAMPLE 28

(−)-3a-(3,4-Dichlorophenyl)octahydro-2-methyl-4,7-methano-1H-isoindole, hydrochloride A 0.653 g portion of 3a-(3,4-dichlorophenyl)octahydro-2-methyl-4,7-methano-1H-isoindole in 25 ml of ethyl acetate is combined with 0.810 g of di-p-toluoyl-l-tartaric acid monohydrate in 25 ml of ethyl acetate. The resultant crystals are collected by filtration to give the (1:1) salt. This salt is combined with water and sodium hydroxide and the resultant amine is extracted with ether. The ether solution is dried and then saturated with hydrogen chloride, giving the desired (−) product.

EXAMPLE 29

(−)-3a-(3,4-Dichlorophenyl)octahydro-4,7-methano-1H-isoindole, hydrochloride

By the method of Example 26, (−)-3a-(3,4-dichlorophenyl)octahydro-2-methyl-4,7-methano-1H-isoindole is reacted with ethyl chloroformate in toluene to give the corresponding 3a-(3,4-dichlorophenyl)octahydro-4,7-methano-2H-isoindole-2-carboxylic acid, ethyl ester. This urethane is hydrolyzed with hydrochloric acid and the solution is evaporated to give (−)-3a-(3,4-dichlorophenyl)octahydro-4,7-methano-1H-isoindole hydrochloride as colorless crystals.

In a like manner, (+)-3a-(3,4-dichlorophenyl)octahydro-2-methyl-4,7-methano-1H-isoindole gives (+)-3a-(3,4-dichlorophenyl)octahydro-4,7-methano-1H-isoindole as colorless crystals.

We claim:

1. A compound selected from the group consisting of an optical isomer of the formula:

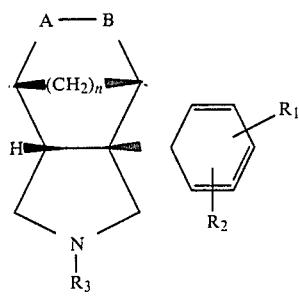

the mirror image thereof and the racemic mixture of the optical isomers wherein n is an integer from 1 to 3; the moiety —A—B— is —CH=CH— or —CH$_2$CH$_2$—; R$_1$ and R$_2$ are each individually selected from the group consisting of hydrogen, hydroxy, alkyl having up to 3 carbon atoms, alkoxy having up to 3 carbon atoms, nitro, halo, trifluoromethyl, amino and azido with the proviso that R$_1$ and R$_2$ may not both be nitro, trifluoromethyl or azido; R$_3$ is hydrogen or alkyl having up to 3 carbon atoms; R$_1$ and R$_2$ taken together are adjacent methylenedioxy or —CH$_2$CH$_2$CH$_2$CH$_2$—; and the pharmacologically acceptable acid-addition and lower alkyl quaternary ammonium salts thereof.

2. The compound according to claim 1; dl-3a-(3,4-dichlorophenyl)-2-methyl-4,7-methano-octahydro-1H-isoindole hydrochloride.

3. The compound according to claim 1; dl-3a-(3,4-dichlorophenyl)-2-methyl-4,7-ethano-octahydro-1H-isoindole fumarate.

4. The compound according to claim 1; dl-3a-(3,4-dichlorophenyl)-2-ethyl-4,7-ethano-octahydro-1H-isoindole fumarate.

5. The compound according to claim 1; dl-3a-(3,4-dichlorophenyl)-4,7-methano-octahydro-1H-isoindole hydrochloride.

6. The compound according to claim 1; dl-3a-(4-chlorophenyl)-4,7-methano-2,3,3a,4,7,7a-hexahydro-1H-isoindole fumarate.

7. The compound according to claim 1; dl-3a-(4-methylphenyl)-2-methyl-4,7-methano-2,3,3a,4,7,7a-hexahydro-1H-isoindole maleate.

8. The compound according to claim 1; dl-3a-(3-methoxyphenyl)-2-methyl-4,7-methano-2,3,3a,4,7,7a-hexahydro-1H-isoindole maleate.

9. The compound according to claim 1; dl-3a-(2-methyl-4,7-methano-2,3,3a,4,7,7a-hexahydro-1H-isoindol-3-yl)phenol.

10. The compound according to claim 1; dl-3a-(3-trifluoromethylphenyl)-2-methyl-4,7-methano-2,3,3a,4,7,7a-hexahydro-1H-isoindole fumarate.

11. The compound according to claim 1; dl-4-(2-methyl-4,7-methano-2,3,3a,4,7,7a-hexahydro-1H-isoindol-3a-yl)benzenamine fumarate.

12. The compound according to claim 1; dl-3a-(4-chlorophenyl)-2-methyl-4,7-methano-octahydro-1H-isoindole fumarate.

13. The compound according to claim 1; dl-3a-(3-chlorophenyl)-2-methyl-4,7-methano-2,3,3a,4,7,7a-hexahydro-1H-isoindole fumarate.

14. The compound according to claim 1; dl-3a-(1,3-benzodioxol-5-yl)-2-methyl-4,7-methano-2,3,3a,4,7,7a-hexahydro-1H-isoindole fumarate.

15. The compound according to claim 1; dl-3a-(3,4-difluorophenyl)-2-methyl-4,7-ethano-octahydro-1H-isoindole fumarate.

16. The compound according to claim 1; dl-3a-(3-bromophenyl)-2-methyl-4,7-methano-octahydro-1H-isoindole hydrochloride.

17. The compound according to claim 1; dl-3a-(3,4-dichlorophenyl)-2-methyl-4,7-propano-octahydro-1H-isoindole hydrochloride.

18. The compound according to claim 1; d-3a-(3,4-dichlorophenyl)-2-methyl-4,7-methano-octahydro-1H-isoindole hydrochloride.

19. The compound according to claim 1; l-3a-(3,4-dichlorophenyl)-2-methyl-4,7-methano-octahydro-1H-isoindole hydrochloride.

20. The compound according to claim 1; d-3a-(3,4-dichlorophenyl)-4,7-methano-octahydro-1H-isoindole hydrochloride.

21. The compound according to claim 1; l-3a-(3,4-dichlorophenyl)-4,7-methano-octahydro-1H-isoindole hydrochloride.

22. A method of treating depression in warm-blooded animals which comprises administering to said animals an antidepressant amount of a compound selected from the group consisting of those of the formula:

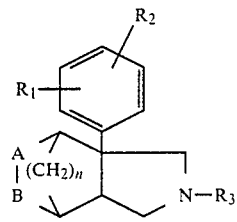

wherein n is an integer from 1 to 3; the moiety —A—B— is —CH=CH— or —CH$_2$CH$_2$—; R$_1$ and R$_2$ are each individually selected from the group consisting of hydrogen, hydroxy, alkyl having up to 3 carbon atoms, alkoxy having up to 3 carbon atoms, nitro, halo, trifluoromethyl, amino and azido with the proviso that R$_1$ and R$_2$ may not both be nitro, trifluoromethyl or azido; R$_3$ is hydrogen or alkyl having up to 3 carbon atoms; R$_1$ and R$_2$ taken together are adjacent methylenedioxy or —CH$_2$CH$_2$CH$_2$CH$_2$—; and the pharmacologically acceptable acid-addition and lower alkyl quaternary ammonium salts thereof.

23. A method of treating stress in warm-blooded animals which comprises administering to said animals a stress alleviating amount of a compound selected from the group consisting of those of the formula:

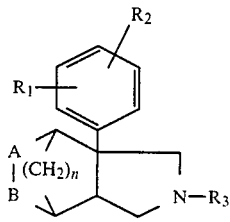

wherein n is an integer from 1 to 3; the moiety —A—B— is —CH=CH— or —CH$_2$CH$_2$—; R$_1$ and R$_2$ are each individually selected from the group consisting of hydrogen, hydroxy, alkyl having up to 3 carbon atoms, alkoxy having up to 3 carbon atoms, nitro, halo, trifluoromethyl, amino and azido with the proviso that R$_1$ and R$_2$ may not both be nitro, trifluoromethyl or azido; R$_3$ is hydrogen or alkyl having up to 3 carbon atoms; R$_1$ and R$_2$ taken together are adjacent methylenedioxy or —CH$_2$CH$_2$CH$_2$CH$_2$—; and the pharmacologically acceptable acid-addition and lower alkyl quaternary ammonium salts thereof.

24. A therapeutic composition of matter in dosage unit form comprising a compound selected from the group consisting of those of the formula:

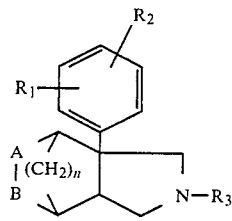

wherein n is an integer from 1 to 3; the moiety —A—B— is —CH=CH— or —CH$_2$CH$_2$—; R$_1$ and R$_2$ are each individually selected from the group consisting of hydrogen, hydroxy, alkyl having up to 3 carbon atoms, alkoxy having up to 3 carbon atoms, nitro, halo, trifluoromethyl, amino and azido with the proviso that R$_1$ and R$_2$ may not both be nitro, trifluoromethyl or azido; R$_3$ is hydrogen or alkyl having up to 3 carbon atoms; R$_1$ and R$_2$ taken together are adjacent methylenedioxy or —CH$_2$CH$_2$CH$_2$CH$_2$—; and the pharmacologically acceptable acid-addition and lower alkyl quaternary ammonium salts thereof in association with a pharmaceutically acceptable carrier.

* * * * *